(12) United States Patent
Katsanevas (10) Patent No.: US 6,237,805 B1
(45) Date of Patent: May 29, 2001

(54) DOOR TOWEL DISPENSER (76) Inventor: Mike J. Katsanevas, 3190 S. Highland Dr., Salt Lake City, UT (US) 84106

( * ) Notice: Subject to any disclaimer, the term of this patent is extended or adjusted under 35 U.S.C. 154(b) by 0 days.

(21) Appl. No.: 09/179,656

(22) Filed: Oct. 27, 1998

Related U.S. Application Data (60) Provisional application No. 60/065,289, filed on Nov. 12, 1997, now abandoned.

(51) Int. Cl.$^7$ ..................................................... A47K 10/24
(52) U.S. Cl. ................................ 221/45; 221/46; 221/47; 221/34
(58) Field of Search .................................. 221/45, 46, 47, 221/48, 49, 61, 63, 34, 97, 197, 281, 287

(56) References Cited

U.S. PATENT DOCUMENTS

| | | | |
|---|---|---|---|
| 4,143,792 | * | 3/1979 | Rex ........................................ 221/97 |
| 4,919,302 | * | 4/1990 | McPherson ............................ 221/34 |
| 5,215,211 | * | 6/1993 | Eberle .................................... 221/1 |
| 5,335,811 | * | 8/1994 | Morand ................................. 221/45 |
| 5,391,339 | * | 2/1995 | Dodge et al. ......................... 221/45 |
| 5,462,197 | * | 10/1995 | Pound ................................... 221/46 |
| 5,630,526 | * | 5/1997 | Moody .................................. 221/45 |
| 5,632,409 | * | 5/1997 | Raghunanan ......................... 221/45 |
| 5,687,875 | * | 11/1997 | Watts et al. ........................... 221/45 |
| 5,765,717 | * | 6/1998 | Gottselig ............................... 221/45 |

* cited by examiner

Primary Examiner—Christopher P. Ellis
Assistant Examiner—Rashmi Sharma
(74) Attorney, Agent, or Firm—Marcus G. Theodore (57) ABSTRACT

An improved system for a towelette/napkin dispenser consisting of a two piece unit, the box member is attached together with the back door plate member with two living hinges at the top rear at the top of each side and a rivet or pin holds them together. The device includes a clear body for the dispenser for viewing the action of the towelettes/napkins inside the center of the body for refilling purposes. A bottom access door or box member of the container moveable from an initial position or dispensing position to an upward loading position for insertion of towelettes/napkins upward into the box member, providing a way to insert the towelettes/napkins into the dispenser body and a latch to keep it closed to keep the towelettes/napkins from falling out of the dispenser or box member when in the dispensing position.

15 Claims, 4 Drawing Sheets

DOOR TOWEL DISPENSER

RELATED APPLICATIONS

This application is a continuation-in-part application of the provisional application No. 60/065,289, filed Nov. 12, 1997 entitled "Sani-Door Towellette Dispenser", now abandoned.

BACKGROUND OF THE INVENTION

1. Field

This invention relates to paper towelette or napkin/towel dispensers. More particularly, it relates to a door mounted paper towelette or napkin/towel dispenser system connected or attached to a bathroom door in public rest rooms of restaurants for sanitary purposes, and laboratory and hospital doors where spread of contamination is of concern. It is designed mainly to aid employees or anybody leaving restrooms, sickrooms, or laboratories in preventing their hands from becoming contaminated from the door knob or handle with other people's germs or chemicals when leaving after washing their hands. Owners and operators of restaurants, or those who work in the health services trades, will readily appreciate the use of the door towel dispenser. The present method of opening a bathroom, laboratory, or sickroom door is by twisting a door knob, touching handles or pushing the door with your just-cleaned hands and therefore contaminating them from other people ahead of you who have pushed the door open or opened it with the door knob. At times this can be quite an unpleasant experience.

2. State of the Art

Various constructions and designs of containers or dispensers are known, which are designed to accommodate rolls, stacks or other arrangements, consisting of serially arranged sheet materials especially dry or wet towels or tissues intended for use, for example, by mothers of infants. In this context, it is known that, due to the serially intertwined or seated arrangement of sheet materials, the respective previous or leading one of the sheet materials pulls with the next succeeding one until a portion of the latter projects through an opening provided in the container for the removal of such sheet material. After the preceding or leading sheet material becomes dislodged from the succeeding sheet material, it can be used for its intended cleaning purpose. No device has been found to date that is similar to the Sani-Door Napkin Dispenser, or used for the specific purpose of dispensing a sanitarily packaged napkin for opening bathroom, sickroom, or laboratory doors.

Prior art reveals a number of receptacles for holding and carrying paper napkins and towels, etc. As far as paper towel and napkin carriers or dispensers are concerned, the most common types are metal, plastic, paper boxes, etc. Although the above carriers are the preferred forms, they possess characteristic disadvantages and inconveniences that render them unsatisfactory when it comes to comfort, safety and sanitary usability.

In recognition of these disadvantages, it would be an advancement in the art to provide a sanitarily approved napkin or towelette at the location most convenient for opening a bathroom door with a container-dispenser that holds articles in an efficiently organized and independently accessible manner for dispensing sanitary towelette/napkins when necessary and convenient to the user, as needed.

The following are patents and fields of Prior art for devices that have been found relating to the Sani-Door Napkin Dispenser with some similarities.

U.S. Pat. No. Des. 331,515 dated Dec. 8, 1992 titled Paper Napkin Dispenser, by T. Petterson, teaches an ornamental design of a paper napkin dispenser, as shown and described. It is a napkin dispenser that is wall-mounted with a curved body and a standard paper dispenser opening. This differs from the present art in that the dispenser opening has an elongated elliptical opening which tends to eliminate the snagging and dragging of the paper as it is pulled from the container.

U.S. Pat. No. 4,838,454 dated Jun. 13, 1989 by F. Salzmann et al. teaches a napkin dispenser includes a drawer which slides in and out of a housing and a push plate which also slides in the housing and is spring-based to push the napkins forward. A pair of locks on the rear of the drawer in the preferred napkin dispenser push the plate forward when the drawer is open but pivots to release the push plate when the drawer is closed so that the napkins are not pressed too tightly, even if napkins are overloaded in the drawer when it is open. Similarly, a pair of locks on the push plate apparatus in the alternative napkin dispenser push the plate forward when the drawer is open but pivot to release the push plate when the drawer is closed. This differs from the present art in several ways. One is that the dispenser is a table model dispenser and secondly it is not designed to mount on anything. Thirdly, the dispenser opening is an elongated elliptical type opening where the napkins are held at the outer edges of the napkin, but are released more easily through the smooth opening of the towelette dispenser, of the present art.

U.S. Pat. No. 5,642,836 dated Jul. 1, 1997, by F. Merriweather, Jr., titled Single Piece Towel Dispenser; describes a towel dispenser consisting of a single unitary molded piece having a container with a front, back, right and left sides, and a top, forming a box with an open bottom, arcuate slots in each side, and a bottom member joined to the back with a living hinge. It has opposed tabs extending laterally for riding in the slots, and an access opening for passage of a towel from the interior of the container. The bottom member is movable from the initial position out of the box to a dispensing position with the tabs in the slots for closing the bottom and supporting the towels thereon, and to an upward loading position for insertion of towels upward into the box past the bottom member. This prior art differs from the present invention in that it is not mounted proximate the door handle.

None of the above prior art inventions and patents, either singularly or in combination, are seen to describe the present invention as claimed.

SUMMARY OF THE INVENTION

The invention comprises a towel dispenser system for a door openably attached to a door frame via hinges or slides where the door is opened by a handle. The towel dispenser system comprises a napkin/towel dispenser mounted to the door or door frame via fasteners, screws of hinges. It has a top, bottom and sides defining an internal napkin/towel storage area designed to accommodate rolls, stacks or other arrangements of serially arranged sheets of dry or wet towels. For most operations, dry towels are adequate to protect a users' hand from contamination. However, for use in certain laboratory environments, or where water for hand washing is not available, a wet towel is preferred to remove and prevent contaminants from being spread by a user opening the door.

The side of the dispenser defines dispenser opening such that the sheets of dry or wet towels are aligned and stacked in a manner for dispensing through the dispenser opening. The dispenser is mounted proximate the handle of the door such that a napkin or towel can be withdrawn by a user to cover the handle for assisting in the opening of the door to prevent hand contamination.

The napkin/towel dispenser is openable and refillable so that a new supply of napkins or towels may be added. For serially arranged sheets, tension means may be mounted underneath the serially arranged sheets of dry or wet towels to force the serially arranged sheets toward the dispenser opening.

A towel dispenser system may include a disposal receptacle attached to the door or door frame near the handle into which used napkins or towels are discarded after use.

Preferably, the napkin/towel dispenser is a one-piece unit with a slot in the top to drop the towelette/napkin packages into the dispenser. It generally includes a back plate for mounting to the door or door frame proximate the handle. The dispenser is preferably structured as an openable rectangular box type container. It is hingedly mounted to the back plate in an initial closed or dispensing position removably secured to the backplate with openable securing structure. When the dispenser is emptied, the container is pivoted open in an upward loading position for insertion of towelette/napkins upward into the box container dispenser. The filled container dispenser is then shut for use.

The dispenser is attached to the back plate with fasteners attached to the back of the dispenser. Preferably, the front of the box type container dispenser defines an access opening for passage of a napkin from the interior of the container. The front face of the box container dispenser is generally patterned or colored to suit the preference of a user, and may contain usage instructions.

Two models of the door mounted paper towelette/napkin dispenser are envisioned. One is a one piece unit with a slot in the top to drop the towelette/napkin package into the dispenser. A second and preferred model is made of plastic or metal. It consists of a single unitary container with a back plate containing four evenly spaced ⅜" holes for mounting to a door. It has a rectangular box type container mounted to the back by a living hinge with opposed tabs extending laterally. Thus hinged, the box member moves from an initial position or dispensing position with the tabs in the slots for closing the bottom and supporting the towelette/napkins therein. When empty, it moves to an upward loading position for insertion of towelette/napkins upward into the box member. The loaded box member is then returned to the dispensing position.

Either model is preferably assembled as one unit with the two parts attached with two screws or rivets to attach the back cover to the door or door frame. The box shaped container dispenser is then attached thereto on each side and to the top rear on both the left and the right sides. Thus attached, it is allowed to be lifted up for inserting a new package of towelette/napkins. The front or the bottom of the box member contains an access opening for passage of a napkin from the interior of the container. The front face of the box contains the instructions and a decorative and colorfull surface to attract the attention of the user. This device is a multipurpose towelette/napkin or paper towel dispenser device having the necessary assembly structure for uses by hospitals, restaurants, schools, nursing homes and other institutions where sanitary measures must be taken.

This need for the Sani-Door towelette/napkin dispenser is evident to those who own and operate a restaurant business or work in the health services trades. The present method of opening a bathroom, laboratory, or sickroom door is by twisting a door knob, touching handles or pushing the door with your just-cleaned hands and therefore contaminating them from other people ahead of you who have pushed the door open or opened it with the door knob. At times this can be quite an unpleasant experience. The Sani-Door towelette/napkin dispenser is generally located just above the door handle and provides a sanitary method of just pulling out a towelette/napkin and opening the door with the towelette/napkin; thereby preventing the touching of the door or door knob with your freshly washed and cleaned hands. The user may dispose of the used towellette/napkin in a receptacle on or near the door as he leaves the rest room.

Accordingly, several objectives and advantages of the invention are:

a. To provide a method of accessing towelette/napkins to open a door with, while at the same time providing a handy and convenient way to prevent the spreading of germs and bacteria to the food and to other people.

b. To provide a more efficient way of opening a door in a sterile environment after cleaning one's hands in a public rest room.

c. To provide a safer and healthier way to open a restroom door in highly critical food handling and health service institutions.

d. To provide a method of dispensing various sizes of napkins and towels through a dispenser opening that will not grab and tear the paper as it is removed from the dispenser, and that can be removed at will and replaced with other napkins or towelettes, designed for a specific purposes.

e. To provide a more pleasant, easier and faster way of retrieving towelette/napkins from the dispenser and changing the type of paper for different combinations.

f. To provide a method where the user can see if the particular towelette/napkin he wants is in the dispenser, through the transparent sides of the dispenser box, without opening the dispenser and removing the towelette/napkins; also by providing a colored imprint of the directions and purpose that fits in the specifically designed front face, on the outside of the dispenser where it can be seen by the user.

g. To provide a clear plastic window as a built-in indicator to notify the service user when the supply has run out for a particular towelette/napkin.

h. To minimize the spread of contaminants by a user wiping one's hands before leaving a contaminated area.

Further objects and advantages are to provide a device that can be easily assembled and manufactured in order to keep the price of the unit reasonable for the consumer. Still further objects and advantages will become apparent from a consideration of the ensuing description and drawings.

LIST OF REFERENCE NUMERALS

10. Main body top of Towelette Dispenser 4" long, 5" wide, 2" deep and ⅛" to ³⁄₁₆" thick.

11. Main body of the Towellette Dispenser, made of plastic or metal, and specifically designed by type of trade or purpose.

12. Hinge and extended ears for the hinge rivets or connector pins.

13. Face of front of main dispenser box or body.

14. Dispenser opening specially designed elongated elliptical opening with smooth rounded edges.

15. Towelette/Napkin, featuring a specifically treated and folded designed napkin or towel for the said purpose.

16. Thickness of main dispenser box body approximately ⅛".

17. Logo printed or embossed on face of main body.

18. Bottom of main dispenser box body.

19. Left hinge ear with typical hinge pin hole.

20. Door mounting plate or base of dispenser.

21. Base typical mounting plate hole, for ⅜" screw.

22. Base mounting plate thickness ⅛".

23. Contact edge of dispenser box with base.

24. Interior of dispenser back base plate.

25. Lower typical mounting plat hole for ⅜" screw.

26. Positive leaf spring for pushing towelette/napkins forward to dispenser opening.

27. Retaining clip for keeping box dispenser from opening.

28. Bottom of dispenser box body.

29. Securing structure surrounding a portion of the dispenser opening.

30. Cylindrical canister of rolled wet tissue dispensed through the bottom of the canister.

31. Wet tissue sheet extending from canister.

32. Dispenser fill opening.

33. Hinged top.

34. Collection bin.

35. Handle slot.

36. Handle.

DESCRIPTION OF THE ILLUSTRATED EMBODIMENTS

Figure 1:
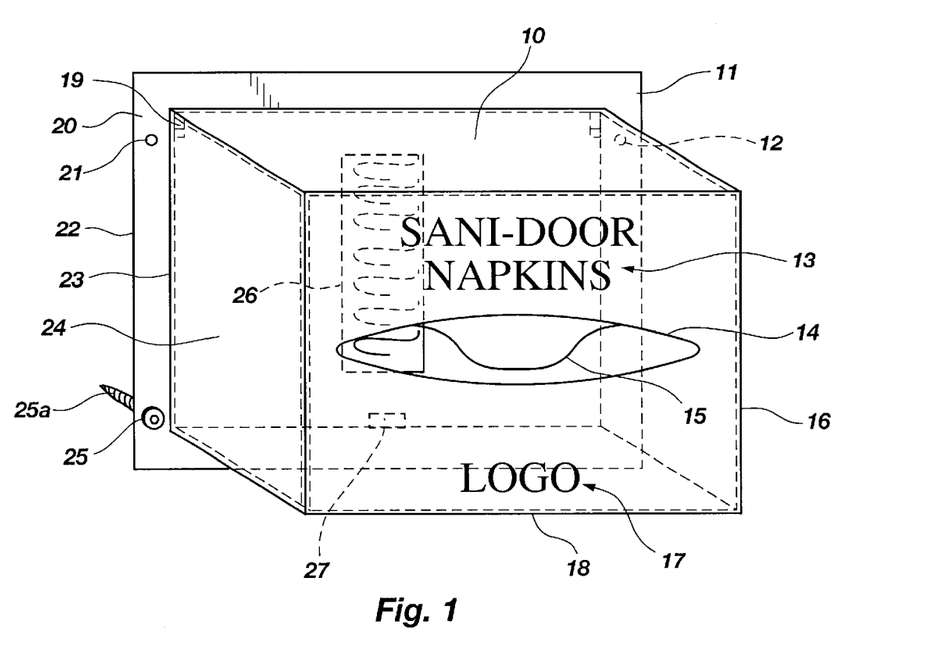
FIG. 1. is a schematic illustration of the dispenser.
Figure 2:
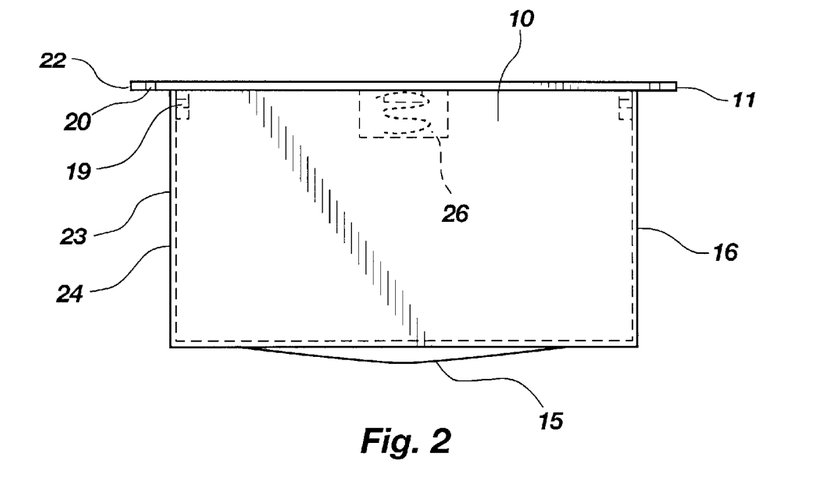
FIG. 2. top view of the dispenser.
Figure 3:
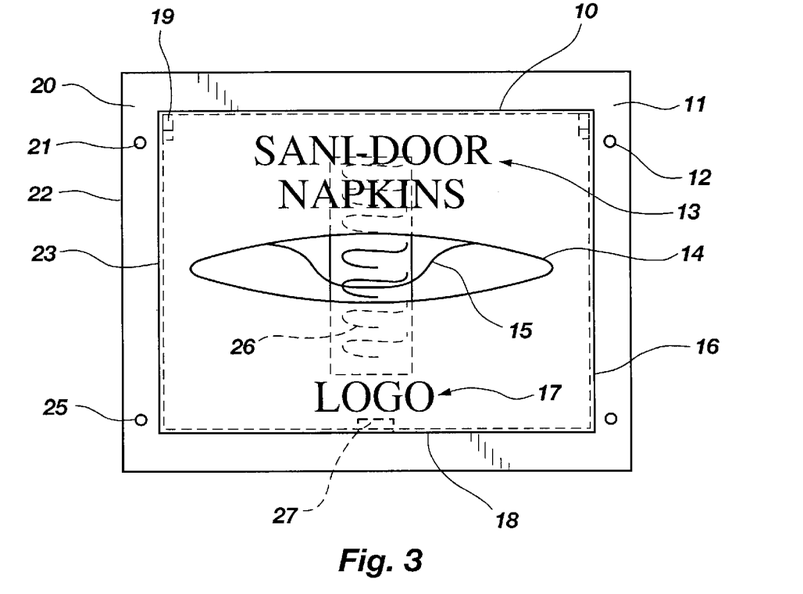
FIG. 3. front view of the dispenser.
Figure 4:
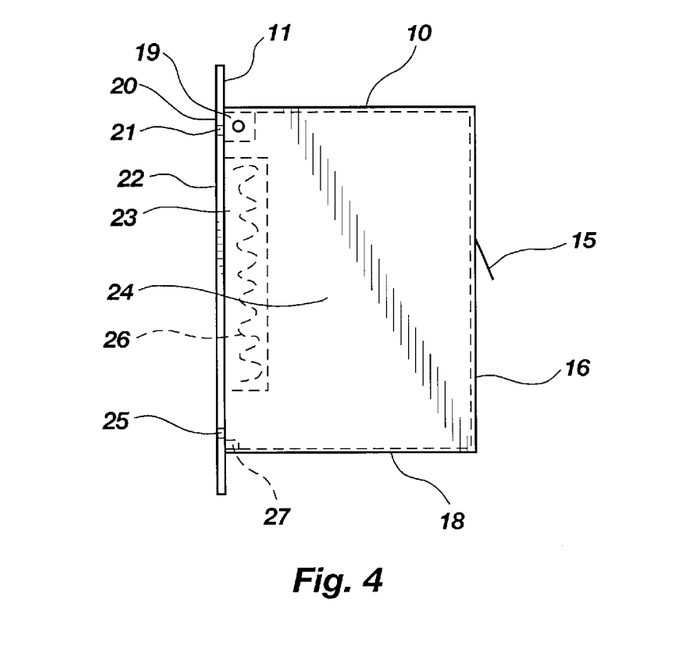
FIG. 4. side view of the dispenser.

A typical embodiment of the door towel dispenser system, of the present invention is illustrated in FIGS. 1 and 3 (front views), FIG. 2 (top view), and FIG. 4 (side view). The door towel dispenser system operates on pulling pressure only. The typical pressure is regulated not to exceed 20 lbs. per square inch. The preferred door towel dispenser main body 10 is a nylon plastic or metal box 5 inch in width and 4 inches high by 2 inches deep and ⅛ inch thick or ³⁄₁₆" thick. The main body 10 is hingedly attached to a base 11 of the door towel dispenser 10. The hinge 12 has extended ears for the hinge rivets or connector pins inserted through the hinge pin ears. The hinge 12 is also attached to the back mounting plate 20. The front face of the dispenser 13 has an imprint in black or color approximately 3" wide, it contains the name and purpose of the towelette/napkins & the logo 17 of the Company. The dispenser opening 14 is a smooth elliptical opening designed to keep the towelette/napkin 15 from snagging when being pulled out, and yet keeps it from falling out. The dispenser is constructed of lexan, with a thickness 16 of about ⅛" thick for strength and durability. The bottom of the main dispenser box 18 as shown, contains the retainer clip 27, which keeps the dispenser box 10 closed during operation. A retainer spring is attached to the back plate 20 and connects to the retainer clip 27 when the dispenser box 10 is closed. The back plate base is attached to the back of the towelette/napkin dispenser 13 to allow the body to hinge and open up at 23 for reloading 15. The left side panel of the dispenser box 24 is connected to the back plate by 2 short ½" bolts or rivets to the back and top side of the back 20 hinge ears 19. The back plate or base is fastened to the door by four ½" screws through the ⅜" holes 21 and 25 on the left and right sides of the base plate 20. The positive action spring 26 is attached to the center of the back base plate 20 by a ¼"×³⁄₁₆" screw, which helps push the towelettes/napkins forward to the dispenser opening.

The device 10 is made of a clear body for the dispenser for viewing the action of the towelettes/napkins inside the center of the body for refilling purposes. A bottom access door or box-like main body 18 of the container 11 is moveable from an initial position or dispensing position to an upward loading position for insertion of towelettes/napkins upward into the main body 18, providing a way to insert the towelettes/napkins into the dispenser body and a latch 27 to keep it closed to keep the towelettes/napkins from falling out of the dispenser 10 when in the dispensing position. This dispenser system is preferably built of heavy gauge lexan and polyurethane plastics and will provide many days of comfortable, convenient, and sanitary use to the consumer.

Figure 5:
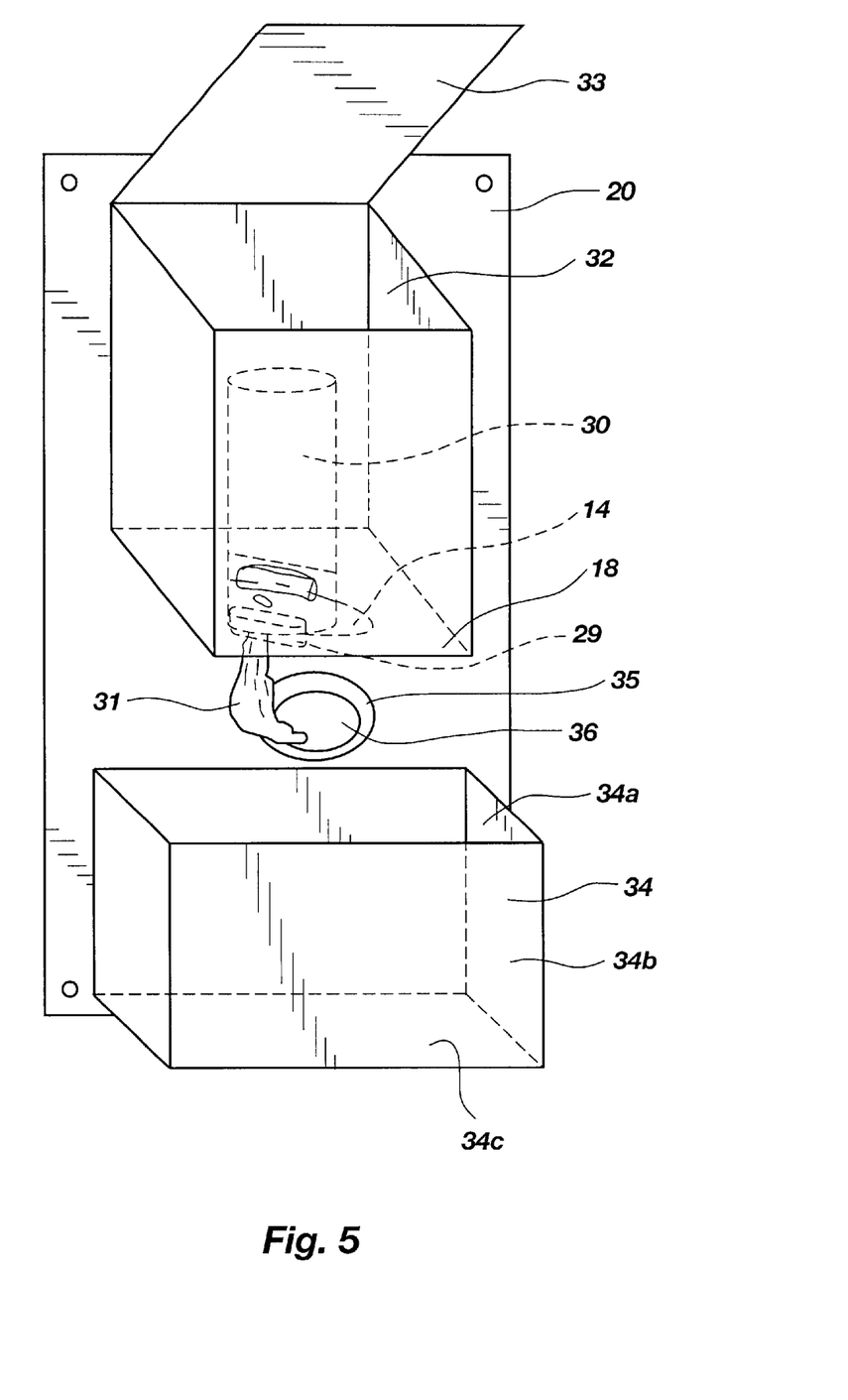
FIG. 5 is a perspective view of another preferred embodiment of the dispenser

FIG. 5 illustrates a perspective view of another embodiment of the invention, with the dispenser opening 14 placed in the bottom 18 of the dispenser 10. Surrounding the dispenser opening is securing structure 29 adapted to secure therein a cylindrical canister 30 containing a roll of wet tissue, which, when dispensed, are pulled down over the handle by a user to open the door. These wet tissues 31 are soaked in an alcohol based rapid drying lotion formulae designed to remove contaminants from the hands. They are particularly used in areas where there is no sink to wash the hands, or it is imperative to insure that the hands are washed a second time to prevent the spread of contaminants from a lab or hospital sick room. The securing structure 29 is adapted around a similar oval dispenser opening 14 described above, such that the dispenser can still be used to dispense stacked dry tissues as well. To fill the dispenser 10, the top 33 is hinged to the base mounting plate 20 to cover the open top 32 into which are placed wet or dry tissues. This dual purpose dispenser embodiment offers the flexibility of adapting to the dispenser to the changing uses of a room.

As shown in FIG. 5, a collection bin 34 may be removably mounted proximate the handle 36 to collect discarded tissues. The collection bin 34 having an open top 34a, sides 34b, and bottom 34c is removably mounted to aid in emptying the same. If the bin 34 is secured to the mounting plate 20, a handle slot 35 is included so that the unit may fit over the handle 36 before securing to the door or frame. After one opens the door by the tissue covered handle 36, the tissue is discarded into the bin 34 upon leaving. Thus the collection bin 34 may be mounted on either side of the door to collect discarded tissues.

Figure 6:
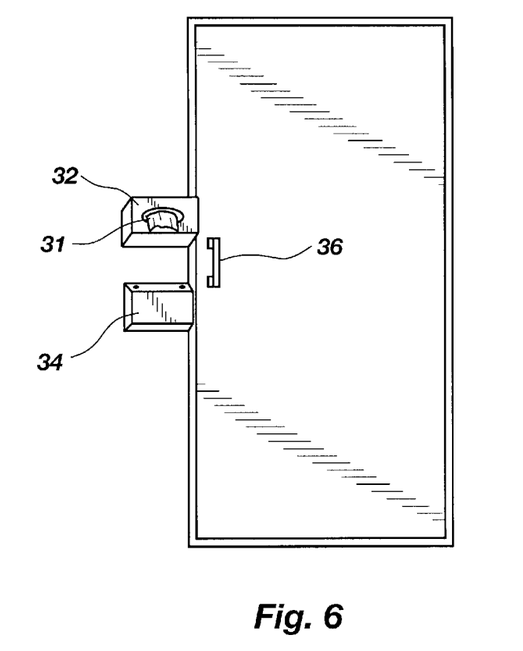
FIG. 6 is a perspective view of another embodiment of the invention.
Figure 7:
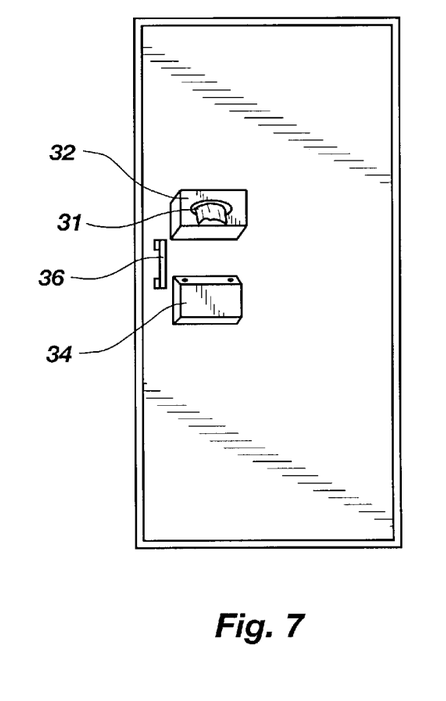
FIG. 7 is a perspective view of still another embodiment of the invention.

FIG. 6 illustrates a tissue dispenser 32 mounted to the wall proximate the door handle 36, with the collection bin 34 mounted underneath to collect discarded tissues 31. FIG. 7 illustrates the tissue dispenser 32 and collection bin 34 mounted to the door itself Accordingly, the reader will see that the Towel Dispenser provides a safe and convenient way to handle opening restroom doors for the specific trades or establishments and may be adapted to other types of trades or institutions as necessary. Furthermore, the Towelette Dispenser has the additional advantage in that; it uses components that are available on the market, making it inexpensive to manufacture and assemble.

It is a device that is needed in every commercial establishment that uses for a specific trade and/or a variety of health institutions and the ease and flexibility of the changing or reloading of the towelette/napkins.

It is a device that is compatible with all types and brands of towelette/napkins, or specifically designed napkins and is designed to handle larger and or shorter sizes.

It is a device that is versatile in that it can be used as a napkin or towel when and where they are needed or when towelette/napkins of a particular purpose are installed in it through the base.

It is a device that does not use electrical power to operate and therefore can be mounted in areas where a source of electrical power is not available. It also does not have to be located near a water source for hand washing, if wetted tissues are stored therein and dispensed.

Although the description above contains many specifics, they should not be construed as limiting the scope of the invention but as providing illustrations of some of the presently preferred embodiments of the invention. Thus the scope of the invention should be determined by the appended claims and their legal equivalents rather than the descriptions of the examples given.

I claim:

1. A towel dispenser in combination with a door having a door handle by which it is opened and closed, openably attached to a door frame and wall, consisting of:
   a. a napkin/towel dispenser mounted to the door, door frame, or wall with securing structure adapted to secure the dispenser on the door within reach of the door handle, having a top, bottom and sides defining an internal napkin/towel storage area designed to accommodate rolls, stacks or other arrangements of serially arranged sheets of towels with at least one of the sides defining a dispenser opening such that the sheets of towels are aligned and stacked in a manner for dispensing through the dispenser opening in the proximity of the handle of the door such that a towel can be withdrawn by a user in a manner to cover the door handle for assisting in the opening of the door to prevent hand contamination, and
   b. a disposal receptacle having a top, bottom, and sides defining an opening leading into an internal collection bin, said receptacle attached with mounting structure to the door, door frame, or wall near the door handle into which used napkins or towels are discarded after opening the door and use.

2. A towel dispenser according to claim 1, wherein the dispenser is structured and mounted to extend towels over the handle.

3. A towel dispenser according to claim 1, wherein the napkin/towel dispenser is openable and refillable.

4. A towel dispenser according to claim 1, including tension means mounted underneath the serially arranged sheets of dry or wet towels to force the serially arranged sheets toward the dispenser opening.

5. A towel dispenser according to claim 1, wherein the disposal receptacle is removably attached to the door to aid in emptying the receptacle when full.

6. A towel dispenser, wherein the napkin/towel dispenser is a one-piece unit with an opening in the top to drop the napkin/towel packages into the dispenser.

7. A towel dispenser according to claim 6, including a back plate for mounting to the door, and wherein the dispenser is an openable rectangular box type container hingedly mounted to the back plate in an initial closed or dispensing position removably secured to the backplate with openable securing structure, and openable in an upward loading position for insertion of towelette/napkins upward into the box container.

8. A towel dispenser according to claim 7, wherein the dispenser is attached with fasteners attached to the back of the dispenser.

9. A towel dispenser according to claim 8, wherein the front of the box type container defines an access opening for passage of a napkin from the interior of the container.

10. A towel dispenser according to claim 9, wherein the front face of the box is patterned or colored to suit the preference of a user.

11. A towel dispenser in combination with a door having a door handle by which it is opened and closed, the door openably attached to a door frame and wall, consisting of:
    a. a base mounting plate defining an opening to accommodate the door handle mounted to the door, such that the base mounting plate accommodates the door handle,
    b. a napkin/towel dispenser mounted to the base mounting plate above the door handle, having an open top, back, bottom and sides defining an internal napkin/towel storage area designed to accommodate serially arranged disposable sheets of napkins/towels, the bottom of the dispenser positioned in the proximity of the door handle and defining a dispenser opening such that the sheets of towels are aligned and stacked in a manner for dispensing through the dispenser opening so a napkin/towel can be withdrawal by a user to cover the door handle when opening the door by the door handle to prevent hand contamination, and
    c. a disposal receptacle having a top, bottom, and sides defining an opening leading into an internal collection bin, said receptacle attached to the bracket near the door handle into which used napkins/towels may be discarded after use.

12. A towel dispenser according to claim 11, including a hinged top attached to the back to open in a first mode to allow filling of the storage area, and to close in a second mode to cover the open top securing towels placed therein.

13. A towel dispenser according to claim 11, including securing structure surrounding the dispenser opening to secure within the dispenser opening a canister of rolled wet towels aligned to dispense wet towels through the dispenser opening.

14. A towel dispenser according to claim 11, including a disposal receptacle having a top, bottom and sides defining an opening leading into an internal collection bin, attached to the door, door frame, or wall near the handle into which used napkins or towels are discarded through the opening into the bin after use.

15. A towel dispenser according to claim 11, wherein the dispenser is structured and mounted to extend towels over the handle.

* * * * *

UNITED STATES PATENT AND TRADEMARK OFFICE
CERTIFICATE OF CORRECTION

PATENT NO.        : 6,237,805 B1
APPLICATION NO. : 09/179656
DATED             : May 29, 2001
INVENTOR(S)       : Mike J. Katsanevas

It is certified that error appears in the above-identified patent and that said Letters Patent is hereby corrected as shown below:

Column 7,
Line 4, change "consisting of" to -- comprising --.

Column 8,
Line 1, after "towel dispenser" add -- according to Claim 1, --.

Signed and Sealed this

Twenty-seventh Day of June, 2006

JON W. DUDAS
*Director of the United States Patent and Trademark Office*

UNITED STATES PATENT AND TRADEMARK OFFICE
CERTIFICATE OF CORRECTION

PATENT NO. : 6,237,805 B1 Page 1 of 1
APPLICATION NO. : 09/179656
DATED : May 29, 2001
INVENTOR(S) : Mike J. Katsanevas It is certified that error appears in the above-identified patent and that said Letters Patent is hereby corrected as shown below:

Column 7,
Line 34, change "consisting of" to -- comprising --.

Column 8,
Line 1, after "towel dispenser" add -- according to Claim 1, --.

This certificate supersedes Certificate of Correction issued June 26, 2006.

Signed and Sealed this

Twelfth Day of September, 2006

JON W. DUDAS
*Director of the United States Patent and Trademark Office*